United States Patent [19]

Martens et al.

[11] Patent Number: 5,279,295
[45] Date of Patent: Jan. 18, 1994

[54] NON-INVASIVE OXIMETER ARRANGEMENT

[75] Inventors: Gerhard Martens, Henstedt-Ulzburg; Jürgen Kordts, Norderstedt; Thomas Helzel, Kaltenkirchen, all of Fed. Rep. of Germany

[73] Assignee: U.S. Philips Corporation, New York, N.Y.

[21] Appl. No.: 616,449

[22] Filed: Nov. 20, 1990

[51] Int. Cl.$^5$ .............................................. A61B 5/00
[52] U.S. Cl. .................................. 128/633; 128/666; 356/41
[58] Field of Search ............... 128/633, 634, 664, 665, 128/666-7; 356/40, 41

[56] References Cited

U.S. PATENT DOCUMENTS

| | | |
|---|---|---|
| 3,461,856 | 10/1965 | Polanyi . |
| 3,998,550 | 12/1976 | Konishi et al. . |
| 4,621,643 | 11/1986 | New, Jr. et al. .................... 128/633 |
| 4,807,630 | 2/1989 | Malinouskas .................... 128/633 |
| 5,035,243 | 7/1991 | Muz .................................. 128/633 |
| 5,058,587 | 10/1991 | Kohno et al. .................... 128/633 |
| 5,070,874 | 12/1991 | Barnes et al. .................... 128/633 |

OTHER PUBLICATIONS

Nellcor Pulsoximeter, Model N-100E, pp. 27, 28, 39 and 40, by Drager, Sep. 1986.

*Primary Examiner*—Kyle L. Howell
*Assistant Examiner*—Angela D. Sykes
*Attorney, Agent, or Firm*—Jack D. Slobod

[57] ABSTRACT

A sensor includes a pair of resiliently loaded jaws for receiving a finger, the sensor including a pair of fiber optic light transmitting guides secured in fixed spaced relation to one of the jaws for sensing blood in the finger tip. A control unit includes a light generator for transmitting light modulated at first and second frequencies to one of the guides via a light guide transfer section. The finger pulse modulates the received transmitted light. The modulated light is sensed by the other guide and returned to a receiver in the control unit via the transfer section for separating and demodulating the different frequency signals. The control unit includes a calculating unit which has two branches for processing and then combining by dividing the processed demodulated signals for determining the oxygen content of the blood from the relative magnitudes of the pulse-dependent modulation factor of the wave reflected from the finger.

17 Claims, 3 Drawing Sheets

NON-INVASIVE OXIMETER ARRANGEMENT

BACKGROUND OF THE INVENTION

1. Field of the Invention

The invention relates to a non-invasive oximeter arrangement with a clamp-like sensor for a finger, a self-calibrating control unit for generating and processing two electromagnetic waves of specific wavelength and an interposed transfer stretch.

2. Description of the Prior Art

Arrangements of this type are generally used in order to monitor the oxygen saturation in human blood, for example as a check on the vital functions of anaesthetized patients. With the aid of optical scatter measurements on body parts through which there is flow close to the surface, such as for example earlobes or fingertips, a measure of the absorption coefficient of the blood is obtained. The magnitude of the absorption coefficient of blood is greatly dependent on the oxygen content in the case of red light and is almost independent thereof in the case of light in the near infrared range. By measuring the intensity ratio of the light in the two wavelength ranges, a measure of the oxygen saturation of the blood can be obtained.

However, when using this measurement principle, considerable sources of interference and sources of error have been found. Thus, the optically measurable signal is for example greatly dependent on the coupling factors of the optical transmitter and of the receiver to the skin surface, so that the application of the sensor, for example on a finger, is extremely sensitive to movement. Furthermore, the optically measurable signal is dependent on the magnitude of the optically recorded blood volume in the body tissue in question. In addition, for an exact quantitative recording of the oxygen content, knowledge of the ratio of the tissue absorptions, that is to say without blood, is necessary for both wavelength ranges.

An oximeter arrangement is known from the instructions for use of the "Nellcor Pulsoximeter, Modell N-100E, pp. 27, 28, 39 und 40", which is a German translation by Dräger Werke AG, Lübeck, September 1986, of the "USERS MANUAL" A 2044, REV A, of the company Nellcor Incorporated, Hayward, Calif., and this oximeter arrangement consists of a clamp-like sensor, an electrical signal transfer section and a signal-processing unit with a microprocessor and displays. The clamp-like sensor has hollow regions which partially receive a finger, the hollow regions are formed by elastic synthetic material and in each case have a window of transparent material, behind which there is arranged in the upper clamp part a double LED and in the lower clamp part a photodiode of large surface area. The LEDs transmit red light in the region of 660 nm and light in the infrared region of 920 nm into the perfused tissue. The portion of the light which is absorbed by the tissue and the non-pulsating blood is different for both wavelengths. However, this portion does not significantly alter during a pulsation. The transmitted residual light is picked up by the photodiode. When the pulsating portion has momentarily disappeared, this intensity represents the initial intensity or reference intensity for the pulsating portion of the absorption. When the pulsating component is present, then the light received by the photodiode at both wavelengths is further reduced by the amount which is absorbed by the pulsating blood at the specific wavelength. With this intensity at both wavelengths, together with the initial intensities at both wavelengths, the ratio of oxygenated blood to the total blood is determined in the control unit. This known oximeter arrangement is expensive and is not suitable for completely solving the abovementioned problems, such as, for example, operating in a strongly electromagnetically disturbed environment in a manner free from interference and safe for the patient. In addition, there is movement sensitivity with respect to the coupling factor, and the effects of extraneous light can falsify the measured result, and there is also the mutually moveable arrangement of the optical transmitter and the optical receiver.

Particularly in view of the important clinical use of treatments involving strong electromagnetic sources, such as, for example, magnetic resonance imaging, in which the use of an oximeter arrangement for monitoring the vital functions of anaesthetized patients in th magnetic resonance imager plays an especially important role, it is extremely important to use an arrangement which, on the one hand, does not disturb the homogeneous electromagnetic field of the imager and, on the other hand, rules out any risks to the patient, such as burn injuries or electric shocks, which can occur as a result of induction, for example in electrical supply lines. This known oximeter arrangement does not satisfy these requirements.

SUMMARY OF THE INVENTION

The present invention is based on the object of providing a non-invasive oximeter arrangement with a clamp-like sensor, for example for a finger, which arrangement is suitable for detecting the degree of oxygen saturation in the blood, and is moreover compatible with the electromagnetically influenced environment, for example the inside of a magnetic resonance imager and is also robust with respect to other sources of interference and sources of error.

This object is achieved according to the invention in that the sensor and the signal transfer section resilient of non-metallic material, the sensor has a spring device and at least one hollow region with an end section adapted to receive a finger tip, in which end section light guide sections terminate and are connected releasably, for non-movement-sensitive connection of the finger, to the sensor-side ends of the transfer section. The transfer section comprises two light wave guides of different cross-section. A control unit has a transmitter, a receiver and a calculating unit for determining the oxygen content of the blood from the relative magnitude of the pulsation-dependent modulation factor of the electromagnetic waves reflected from the finger, differently coded, corresponding to the spectral windows of the signal transfer section.

According to a preferred embodiment of the invention, the first optical guide conveys the electromagnetic waves, hereinafter also referred to for brevity as waves, from the control unit to the sensor and the second optical guide conveys the electromagnetic waves reflected from the finger back to the control unit, in which respect the second guide has a larger cross-section than the first guide. Both guides are made of plastic and in the sensor are connected to the light guide sections via a plug device. The fact that these light guide sections are arranged in the sensor in a fixed relative speed arrangement prevents movement errors arising from relative moments of the two guides of the signal transfer section during operation.

It can also be advantageous for the sensor to have an upper part and a lower part, in each case with a groove-shaped hollow region for receiving part of the finger, which upper part and lower part are moveable with respect to each other in the manner of a clamp and by held clamped a resilient element. The lower hollow region advantageously has an inner end section adapted to receive the fingertip, in which end section the light guide sections are arranged with their crosssectional surfaces flush and spaced from each other. The distance of the cross-sectional surfaces from each other essentially serves to prevent optical short circuits.

According to the invention, the crosssectional surfaces are arranged relative to each other at an angle corresponding to the curvature of the end section, and the light guide sections are embedded in a casting composition. They extend in a partial curve towards the fingertip. The hollow regions can consist of flexible material for adaptation to different shapes of fin a both cross-sectional surfaces in one of the hollow regions, namely the lower one, it is again possible to prevent movement errors occurring as a result of inadvertent movements of the two clamp parts relative to each other.

The resilient element is advantageously a rubber band loading the finger and applied around the upper part and lower part of the sensor, or a springy foam material which, with the same effect, is between corresponding parts of the sensor for forcing opposite ends of the sensor together.

According to a preferred embodiment, the transmitter has an LED (light emitting diode) for each of the first and second electromagnetic waves which LEDs are supplied from a block circuit for generating differently modulated corresponding signal. One light guide is allocated to each LED, which light guide leads on the input side into an optical coupling member at whose output the first guide of the optical transfer section is connected.

The receiver is advantageously connected on the input side to the second guide of the optical transfer section and has a transformer for generating a corresponding electrical signal, downstream of which there is a demodulation circuit with rectifiers, as a result of which there is a demodulated, rectified output signal for each of the two reflected wavelengths. The modulation of the electromagnetic waves serves, inter alia, for the detection of the two electromagnetic waves generated by the transmitter and thus also for the suppression of interferences caused by extraneous light.

The output signals of the receiver are conveyed on the input side to a calculating unit. According to the invention, the latter has two branches, in each branch there is a high-pass filter with a downstream circuit for determining the pulse-dependent amplitude, in other words the pulsation-dependent modulation factor, and a in parallel with the high pass filter a low-pass filter and a first pulse height-calculating member for dividing the second output signal from the downstream circuit by that received from the low-pass filter. Downstream of the two dividing members from each branch is a further member for division at whose output a signal appears for onward conveying to a display or data interface. The output signal can be relayed to a display unit and/or data interface.

According to the invention, a lower first wavelength of 660 nm and an upper second wavelength of approximately 780 nm to approximately 850 nm is used for exploitation of the spectral windows, in which respect the first wavelength is preferably amplitude-modulated at a first frequency and the second wavelength at a second frequency. Compared to a known first wavelength of 660 nm and a second wavelength of 805 nm, a considerably greater range is possible according to the invention for the second.

According to a preferred embodiment, however, it is also possible for the first and second wavelength to be modulated with the aid of a time-division multiplex operation.

A wavelength of approximately 830 nm is preferably used for the second wavelength. Since it can be shown that wavelengths of more than approximately 850 nm are considerably attenuated in the light-conducting fibres used, there is an upper limit on wavelengths.

All the light guides are preferably of singlewire or multiwire construction, in which respect the first guide has a fibre of, for example, 1 mm and the second guide, because of high light losses in the finger, has 32 fibres each of, for example, 0.5 mm diameter.

The oximeter arrangement according to the invention thus uses a pulsed signal for recording the oxygen content of the blood, which signal is superposed on a high equisignal background and depends on the blood volume in the finger in the rhythm of the heartbeat. The modulation factor of this small signal, i.e. the quotient of pulsed alternating signal amplitude and background equals the product of specific absorption of the blood at the wavelength used multiplied by the blood volume pulse, or the change caused by it in the length of the light path in the blood volume. This quotient no longer depends on the tissue absorption and the coupling factor between the cross-sectional surfaces of the fibres and the skin surface. The quotient of the optical pulse signals standardized to their background at the abovementioned wavelengths finally eliminates the unknown quantity of blood volume per pulsation, so that the quotient of specific absorption of the blood at the two wavelengths used is available at the output of the calculating unit as a measure of the oxygen content.

BRIEF DESCRIPTION OF THE DRAWING

Further preferred embodiments of the invention emerge from the subclaims.

One exemplary embodiment is illustrated in greater detail below with reference to the drawing, in which:

FIG. 2b shows a schematic diagram of a peak-value detector of the control unit of the oximeter arrangement of FIG. 2a;

FIG. 1 shows a non-invasive oximeter arrangement 10 according to the invention. It includes of a clamp-like sensor 11, a self calibrating control unit 12 for recording and processing two electromagnetic waves of predetermined wavelength and a light transfer section 13 which preferably comprises two light guides 31, 32 and which connects the control unit 12 to the sensor 11. The control unit 12 has an energy supply 14, a transmitter 15, a receiver 16 and a calculating unit 17 at whose output 18 the signal representing the oxygen content of the blood appears. This signal can be made visible within the control unit 12 via a display (not shown) or else can be supplied for example to a data interface (likewise not shown).

The sensor 11 is designed to be clamp-like and consists essentially of an upper part 19 and a lower part 20, which are movably connected to each other via an articulartion joint 50. The sensor 11 is made completely of non-metallic material and remains in the closed position, without any external leverage, by means of a non-metallic spring device consisting of a rubber band 70 applied around the upper part 19 and lower part 20, or of a springy foam material 71 which is applied between the parts 19 and 20. FIG. 1 shows both possibilities, and FIGS. 4 and 5 show only the rubber band 70. The upper part 19 and the lower part 20 have hollow regions 21 and 22 designed in the form of grooves as clamping jaws. These hollow regions 21 and 22 form a finger bed of preferably soft elastic synthetic material, into which at least part, preferably two phalanges of an index finger (not shown) can be clamped. The lower hollow region 22 pointing inwards into the clamp-like sensor is limited by an end section 23 whose shape is suitable for supporting the fingertip of the finger in a flush manner. In the surface of this end section 23, the cross-sectional end surfaces 51, 52 of two light guide sections 24 and 25 are arranged flush and at a distance from each other, pointing towards the clamped finger. End pieces 26 and 27 can be provided towards the end section 23 for receiving the ends of the light guide sections 24 and 25, which in turn are fixed by means of a casting composition 28. The light guide sections 24 and 25 then lead in a slight curve in each case to a plug device 29 and 30 in the lower part 20 of the sensor 11.

Figure 1:
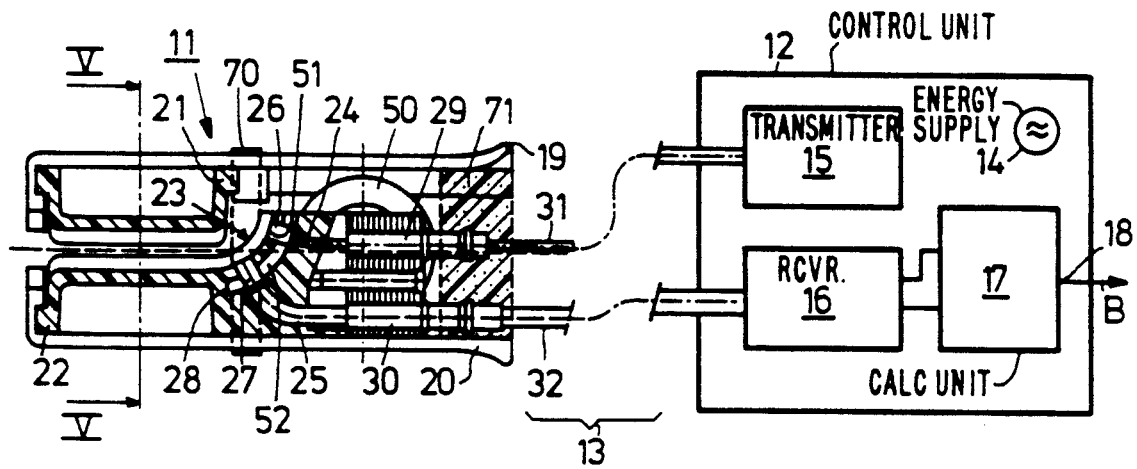
FIG. 1 shows a non-invasive oximeter arrangement according to the invention, in which the sensor is shown in section along its longitudinal axis.

The light guide sections 24 and 25 are, like the guides 31 and 32 of the transfer section 13, commercially available plastic lightwave guides. Guide 31 constitutes a transmission line for the control unit 12 and guide 32 constitutes a receiving line. A fibre of 1 mm diameter is used for example as the transmission line. The large light loss upon transillumination of the finger makes it necessary to provide the receiving line with a larger cross-section. For this purpose, a light wave guide bundle with 32 fibres each of 0.5 mm diameter can be used. Alternatively, one fibre of, for example, 3 mm diameter can of course also be used, but is then very rigid. The guides 31 and 32 are connected via the plugs 29 and 30 to the sensor 11. The electromagnetic waves arriving in the sensor 11 via the guide 31 emerge at the end section 23 and enter the fingertip. By virtue of the fact that the cross-sectional surface of the light guide section 25 likewise terminates in the end section 23, it is at an angle relative to the cross-sectional surface 51 of the light guide section 24 terminating in end section 23. Some of the electromagnetic waves reflected from the finger then pass into the light guide section 25 and via the plug device 30 into the guide 32 and thus into the control unit 12.

The finger is not completely transilluminated by this arrangement. Rather, the feeding in and out of light are both carried out at the fingertip, for which reason both light guides can be applied to the finger rigidly from one side, by which means movement errors, which are caused for example by an altered optical coupling during cable movements, are reduced.

FIG. 2 shows a control unit 12 in which the schematic design of the transmitter 15, receiver 16 and calculating unit 17 is represented.

The transmitter 15 essentially has an optical coupler 33 which is connected on the output side to the guide 31 and on the input side to two further light guides 34 and 35. The light 34 and 35 lead in each case to a respective corresponding LED 36 and 37, supplied in each case with an electrical signal from a circuit 60. For this purpose, the circuit 60 can contain generators 38 and 39. The generator 38 generates a signal for generating an electromagnetic wave of 660 nm, the signal preferably being amplitude-modulated at a frequency $f_1$. The generator 39 generates a signal for generating an electromagnetic wave of preferably 830 nm, the signal being amplitude-modulated at a frequency $f_2$. It should be pointed out here that another modulation (not shown in FIG. 2) can also be provided in the circuit 60, for example a time-division multiplex modulation. Light with a wavelength of approximately 780 nm to approximately 850 nm can also be used as the second wavelength. Larger wavelengths are too greatly attenuated in the plastic fibres, for which reason they are less suitable.

The electromagnetic waves, modulated with respect to their intensity in order to prevent extraneous light influences on the measured result, finally arrive, after reflection in the finger, via guide 32 in the receiver 16 and there at a transducer 40 for generating corresponding electrical signals. The measurement information present at the output of the transducer 40 is selected in a demodulation circuit 61, in the case of amplitude modulation in accordance with FIG. 2 with in each case a downstream filter 41 and 42 corresponding to the modulation frequencies $f_1$ and $f_2$ and a downstream rectification in the rectifiers 43 and 44. After demodulation, there are two signals available at the output of the receiver 16, which signals in each case are proportional to the optical reflection of the finger in the sensor 11. It should be noted here that timing signals are sent from the transmitter 15 to the demodulation circuit 61.

Figure 3:
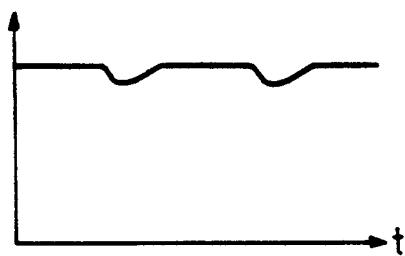
FIG. 3 shows a typical signal shape of a reflected electromagnetic wave at the output of a receiver of the control unit.
Figure 4:
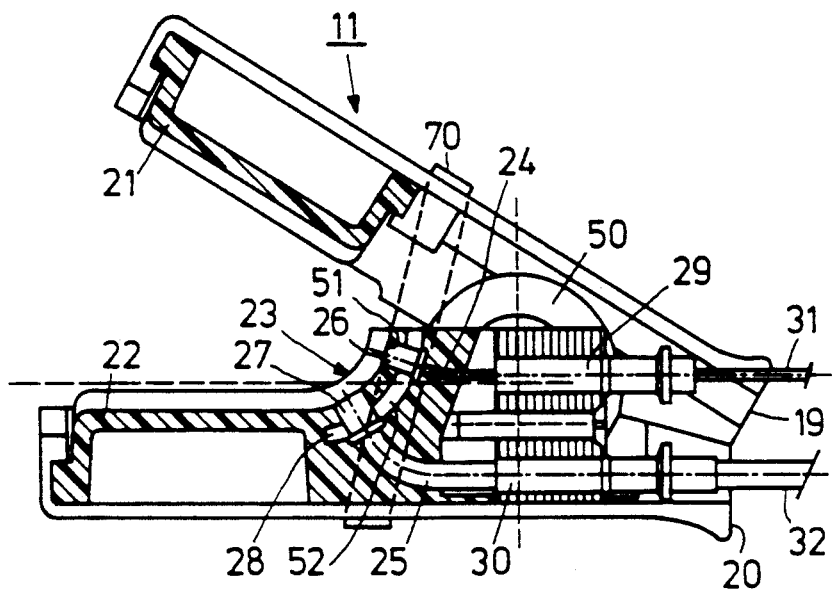
FIG. 4 shows the sensor of the oximeter arrangement according to FIG. 1 in the opened position.
Figure 5:
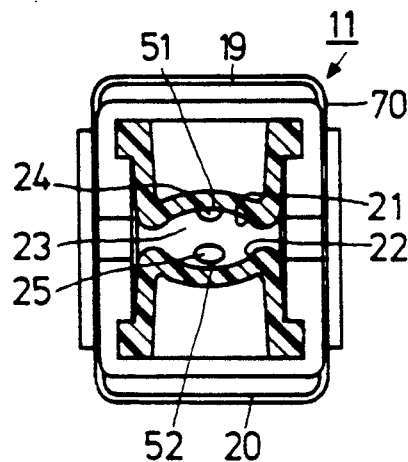
FIG. 5 shows a sectional view along the line V—V of the sensor of the oximeter arrangement according to FIG. 1.

FIG. 3 shows the shape of the signals at the output of the receiver 16. The shape consists essentially of a relatively large signal background on which small signal changes occur in the rhythm of the heartbeat. These signal changes originate from the pulsation in the transilluminated finger. This small pulsed signal is used to record the oxygen content of the blood, since it corresponds to the change in blood volume caused by the action of the heart, that is to say the blood volume pulse, and thus originates principally from the arterial area of the blood circulation and is therefore a preferred source of information for the degree of oxygen saturation. The modulation factor of this small signal, i.e. the quotient of pulse alternating amplitude and background, equals the product of specific absorption of the blood at the wavelength used multiplied by the blood volume pulse, or the change in the length of the light path in the blood volume caused by it. This quotient depends on none of the interference variables mentioned at the outset. In addition, it is independent of the initial intensity of the light source, the attenuation losses on the light guide fibre transfer sections and the properties of the photodiode and of the transformer itself. The quotient of the optical pulse signals standardized to their background at the abovementioned wavelengths finally eliminates the unknown quantity of the volume pulse. The quotient of specific absorption of the blood at both wavelengths used remains as the result and is a measure of the oxygen content.

In the calculating unit 17, to which the output signals from the receiver 16 are supplied as input signals, this quotient, which represents the oxygen content, is determined and is conveyed further as an output signal to a display and/or an interface (not shown) in accordance with arrow B. A branch is allocated to each input signal of the calculating unit, the branch consisting of a highpass filter 45, a downstream circuit 46 for determining the pulse-dependent amplitude, a parallel low-pass filter 47 and a member 48 which is connected to the outputs of the circuit 46 and of the low-pass filter 47. Each member 48 serves for quotient formation for calculating the relative pulse height for each of the two demodulated signals, in other words the division of the height of the pulsed signal, which is formed by the high-pass filter 45 with the downstream circuit 46, by the relatively large signal background which appears at the output of the low-pass filter 47. The output signals of the two members 48 are supplied on the input side to a further member 49. This member 49 is a divider and is used to carry out a division of the two input signals proportional to the relative pulse heights, in order to generate at the output the desired signal which is now dependent only on the oxygen content of the blood.

The circuit 46 can be designed as a peak value rectifier, which may however be susceptible to interference in the case of small signals. It is advantageous to use a circuit 46 with a comparator circuit for determining the pulsation or a corresponding trigger impulse and a minimum-maximum detector with a downstream memory.

Figure 2A:
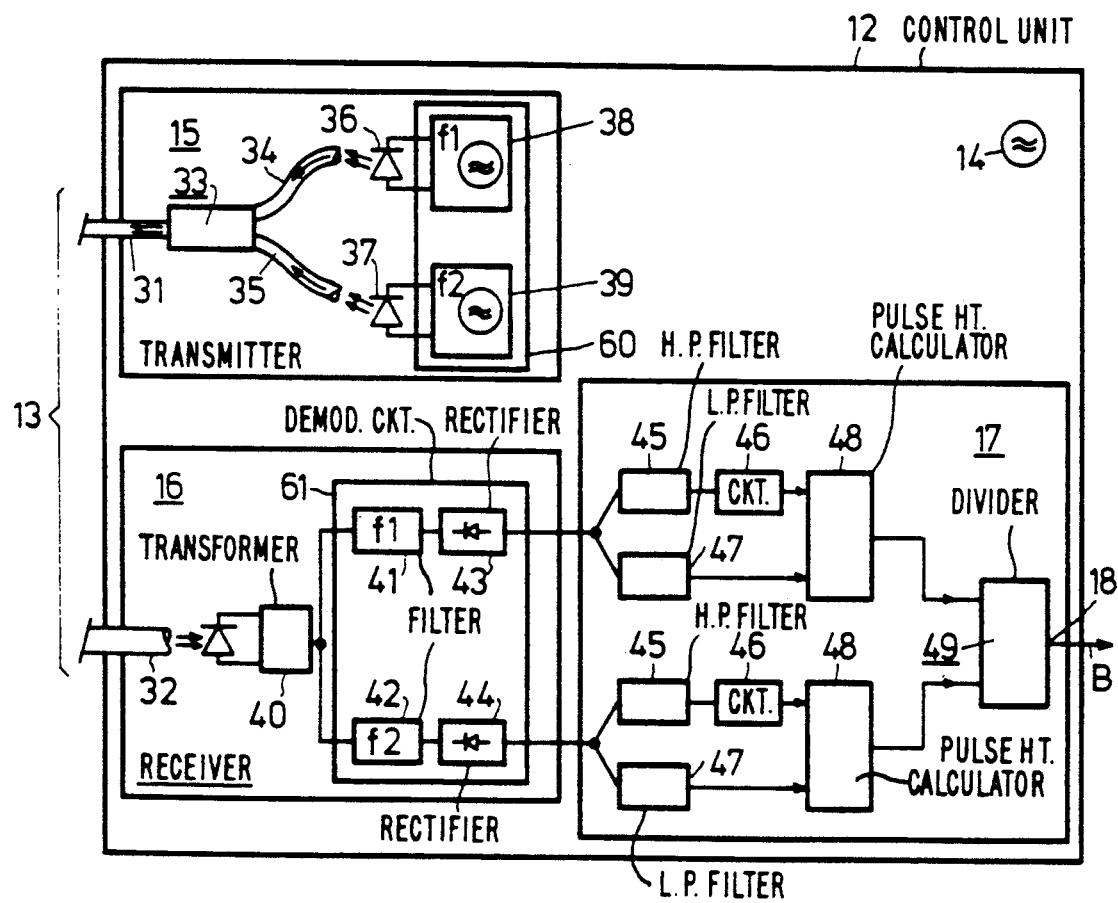
FIG. 2a shows the schematic design of a control unit of the oximeter arrangement.
Figure 2B:
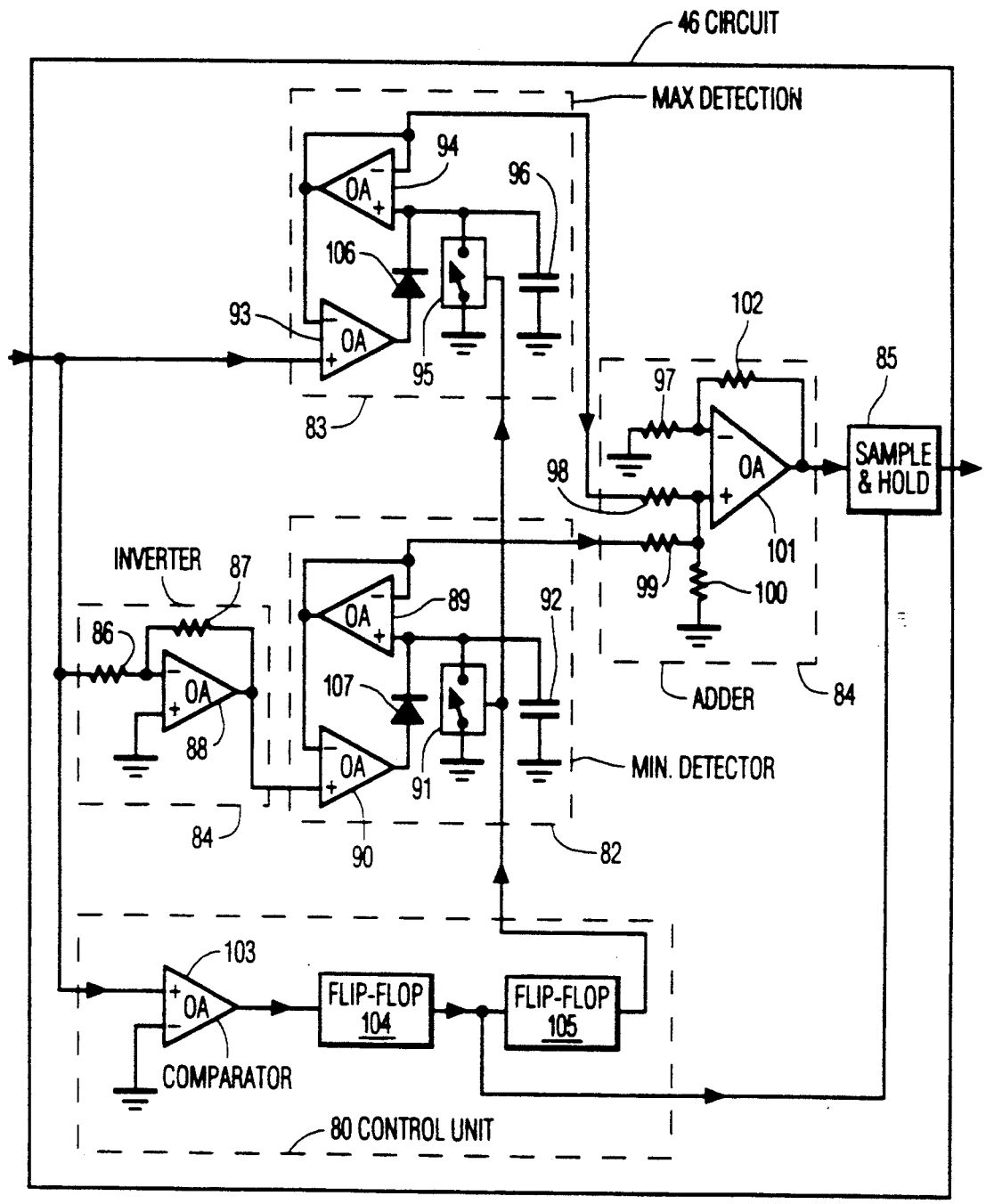

According to FIG. 2b the input of a circuit 46 receives a pulsed blood signal, i.e. the output signal of a filter 45, FIG. 2a, which is processed such that its peak-to-peak value is produced at the output of the circuit 46 as a DC signal. The input signal to circuit 46 controls a control unit 80 that by means of a comparator 103 generates a pulse trigger signal which serves as a switching signal having a frequency which depends on the blood pulse frequency. When a new pulse period starts, the peak-to-peak value determined in the previous period is first stored in sample-and-hold circuit 85 of the circuit 46 with the aid of monostable flip-flops 104 and 105, a short pulse from the flip-flop 104 triggering the storage. Then the flip-flop 105 output pulse signal sets a minimum-detector 82 and a maximum detector 83 to zero. The detector 82 comprises operational amplifiers 89, 90, a diode 107, a switch 91 and a capaciter 92. The detector 83 comprises operational amplifiers 93, 94, a diode 106, a switch 95 and a capacitor 96. These detectors are so-called peak-value detectors which are well known in this art.

The detector 83 detects the maximum value of the input signal applied to the circuit 46. The operational amplifier 93 charges the capacitor 96 via the diode 106 until the voltage across the capacitor 96 corresponds to the amplifier 93 input voltage when the amplifier 93 input voltage increases, the voltage across the capacitor 96 also increases. If the amplifier 93 input voltage decreases, the diode 106 is reversed biased and the previous higher value is maintained at the output of the detector 83. At the start of a new period and after storage by the circuit 85, the detectors 82 and 83 are reset to zero by switches 91 and 95. Inverter 81 (comprising resistors 86, 87 and an operational amplifier 88) preceding the minimum detector 82 applies an inverted input signal to the minimum detector 82. The detector 82 processes the signal at its input in a manner similar to the detector 83 and consequently detects the maximum value of that signal. Because the input signal is inverted by the inverter 81, this maximum value corresponds to the minimum value of the input signal, but with inverted polarity.

By forming the sum of the minimum and maximum values with adder 84 (comprising resistors 97, 98, 99, 100 and 102 and an operational amplifier 101), which is connected at the output of the detectors 82 and 83, a DC signal is generated, which corresponds to the momentary peak-to-peak value of the circuit 46 input signal. At the beginning of a period, after the detectors 82 and 83 have been reset to zero, the output signal of the adder 84 is also zero. A positive half wave at the input to circuit 46 causes the detector 83 to follow until the maximum value is reached, the voltage being maintained constant from then on. The output signal of the adder 84 then increases correspondingly. During the negative half wave, the signal at the input of the detector 82 increases in value due to inversion by the inverter 81. This detector increases its output signal value until the input signal has reached its minimum value. Consequently, the output voltage of the adder 84 further increases in value during the negative half wave and, at the end of the period, the output voltager of the adder is a DC voltage whose value corresponds to the peak-to-peak value of the input signal. This value is stored in the circuit 85 at the beginning of each succeeding period.

In the calculating unit 17, FIG. 2a, two circuits 46 are provided, one for each branch. However, the control unit 80 may be included in only one of the two circuits 46 as its output may be used to control the other circuit 46 of the other branch.

The features of the invention disclosed in the above description, in the figures and in the claims may be essential in their various embodiments both individually and in any desired combination for the implementation of the invention.

What is claimed is:

1. A non-invasive oximeter arrangement comprising:
    a sensor configured for clamping on the end of a finger and including upper and lower clamping means each having a groove-like hollow region for forming a finger bed for receiving a finger, the upper and lower clamping means being moveable relative to each other in clamping relation, and further including a resilient means for placing the upper and lower clamping means in a clamp state; said hollow region of said lower clamping means having an internal end section having a surface for non-movement registration with a region of said finger, said end section having a transmission aperture and a reception aperture therein which are spaced from each other;
    first and second light guide elements carried by the sensor and having respective end surfaces respectively positioned in said transmission and reception apertures, said end surfaces being flush with said surface of said end section of said hollow region of said lower clamping means;
    light transfer means for conveying electromagnetic waves to and from said sensor, said light transfer means comprising a transmission lightwave guide and a reception lightwave guide;

said end section of said hollow region of said lower clamping means being curved, said end surfaces of said light guide elements being arranged at an angle relative to each other corresponding to the curvature of said end section, said light guide elements including light guide sections which are embedded in a casting composition and extend in a curve towards said end section, the hollow regions of said upper and lower clamping means comprising flexible material for adaptation to different finger shapes;

plug means for releasably securing a first end of said transmission lightwave guide and a first end of said reception lightwave guide respectively to said first and second light guide elements; and control means coupled to said sensor by said light transfer means, said control means comprising:

transmitter means for generating two electromagnetic waves at two different wavelengths to be simultaneously applied to said finger at said transmission aperture via said transmission lightwave guide and said first light guide element, said two applied electromagnetic waves resulting in two electromagnetic waves at said two different wavelengths exiting said finger at said reception aperture, the two exiting electromagnetic waves exhibiting pulse modulation due to pulsatile flowing block in the finger;

receiving means for receiving said two exiting electromagnetic waves via said second light guide element and said reception lightwave guide; and calculating means coupled to said receiver means for forming an output signal, indicative of the oxygen content of the blood in the finger, as a function of the relative magnitudes of the pulse modulation of the two exiting electromagnetic waves.

2. The arrangement of claim 1 wherein the resilient means is a rubber material which engages the upper and lower clamping means.

3. The arrangement of claim 1 wherein the transmitter means comprises: first and second LEDs for respectively generating said two applied electromagnetic waves, said first and second LEDs being driven by different first and second modulation waveforms, respectively; third and fourth light guides having first ends respectively coupled to said first and second LEDs, and an optical coupling means for coupling second ends of the third and fourth light guides to said transmission lightwave guide.

4. The arrangement of claim 3 wherein said receiver means comprises: transformer means responsive to the received pulse modulated electromagnetic waves at said two wavelengths for generating an electrical signal; and a demodulation circuit coupled to said transformer means for demodulating the electrical signal generated by said transformer means to produce two rectified signals corresponding to the amplitudes of said received pulse modulated electromagnetic waves at said two wavelengths, respectively.

5. The arrangement of claim 4 wherein said calculating means comprises first and second branches each for receiving a different demodulated signal from said demodulation circuit; each of said branches comprising a high-pass filter and detecting means for determining a dependent amplitude of a received output signal from the high-pass filter, a low-pass filter in parallel with said high-pass filter and said detecting means, and means for dividing a determined pulse-dependent output of said detecting means by an output of said low-pass filter; and a further means responsive to a outputs of the dividing means of both said branches for producing a signal manifesting oxygen saturation.

6. The arrangement of claim 5 wherein one of said waves has a wavelength of approximately 660 nm and the other wave has a wavelength of approximately 780 nm to 850 nm, said transmitter means including means for amplitude-modulating a first wavelength at a first frequency $f_1$ and a second wavelength at a second frequency $f_2$, and said receiver means includes signal demodulating means comprising a pair of serial circuits, each serial circuit being for a different wavelength and comprising a filter and a rectifier.

7. The arrangement of claim 6 wherein said transmission lightwave guide has a single fiber of 1 mm diameter and said reception lightwave guide has a plurality of fibers each of 0.5 mm diameter.

8. The arrangement of claim 5 wherein said transmission lightwave guide has a single fiber of 1 mm diameter and said reception lightwave guide has a plurality of fibers each of 0.5 mm diameter.

9. The arrangement of claim 5 wherein each of said detecting means comprises circuit means including peak value detector means for detecting the peak value of said high pass filter output signal.

10. The arrangement of claim 9 wherein said peak value detector means comprises a minimum-maximum decoder responsive to said high pass filter output signal, memory means for storing an output of said minimum-maximum decoder, and comparator means responsive to said high pass filter output signal and coupled to said minimum-maximum decoder and memory means for generating triggering pulses and applying said pulses to said decoder and to said memory means.

11. The arrangement of claim 10 wherein said peak value detector means includes said comparator means in only one of said branches, the comparator means of the one branch being coupled to the peak value detector means of the other branch for applying said pulses to the other branch.

12. The arrangement of claim 1 wherein one of said waves has a wavelength of approximately 660 nm and the other wave has a wavelength of approximately 780 nm to 850 nm, said transmitter means including means for amplitude-modulating a first wavelength at a first frequency $f_1$ and a second wavelength at a second frequency $f_2$, and said receiver means includes signal demodulation means comprising a pair of serial circuits, each serial circuit being for a different wavelength and comprising a filter and a rectifier.

13. The arrangement of claim 1 wherein one of the waves has a wavelength of approximately 660 nm.

14. The arrangement of claim 13 wherein the other wave has a wavelength of approximately 830 nm.

15. The arrangement of claim 1 wherein said transmission lightwave guide has a single fiber of 1 mm diameter and said reception lightwave guide has a plurality of fibers each of 0.5 mm diameter.

16. The arrangement of claim 1 wherein said calculating means comprises: two branch circuits each including filter means and dividing means for producing an output signal corresponding to the pulse modulation of a respective one of the exiting electromagnetic waves; and dividing means for dividing the output signal of one branch by the output signal of the other branch.

17. The arrangement of claim 1 wherein said transmission lightwave guide is smaller in cross-section than said reception lightwave guide.

* * * * *